United States Patent
Le Coent et al.

(10) Patent No.: US 7,964,611 B2
(45) Date of Patent: Jun. 21, 2011

(54) PROCESS FOR MAKING ALKALINE EARTH METAL BORATED SULFONATES

(75) Inventors: Jean-Louis Le Coent, Le Havre (FR); Pierre Tequi, Breaute (FR); John McDonald, Emeryville, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 23 days.

(21) Appl. No.: 12/334,827

(22) Filed: Dec. 15, 2008

(65) Prior Publication Data

US 2009/0099385 A1   Apr. 16, 2009

Related U.S. Application Data

(62) Division of application No. 11/292,404, filed on Nov. 30, 2005, now Pat. No. 7,479,568.

(51) Int. Cl.
*C07F 5/04* (2006.01)
(52) U.S. Cl. ........................................ 514/297
(58) Field of Classification Search ................. None
See application file for complete search history.

(56) References Cited

U.S. PATENT DOCUMENTS

| | | | |
|---|---|---|---|
| 3,480,548 A | 11/1969 | Hellmuth et el. | |
| 3,679,584 A | 7/1972 | Hellmuth et al. | |
| 4,683,126 A | 7/1987 | Inoue et al. | |
| 4,744,920 A | 5/1988 | Fischer et al. | |
| 4,792,410 A * | 12/1988 | Schwind et al. | 508/186 |
| 4,965,003 A | 10/1990 | Schlicht | |
| 4,965,004 A | 10/1990 | Schlicht et al. | |
| 2005/0202954 A1 | 9/2005 | Campbell et al. | |
| 2005/0203322 A1 | 9/2005 | Harris et al. | |
| 2005/0203323 A1 | 9/2005 | Harris et al. | |

* cited by examiner

*Primary Examiner* — Kamal A Saeed
(74) *Attorney, Agent, or Firm* — Josetta I. Jones

(57) ABSTRACT

An alkaline earth metal borated sulfonate prepared by a process comprising reacting a mixture of the following materials (A) (1) at least one of an oil soluble sulfonic acid or alkaline earth sulfonate salt or mixtures thereof (2) at least one source of an alkaline earth metal; and (3) at least one source of boron, in the presence of a mixture of comprising (4) at least one hydrocarbon solvent; and (5) at least one low molecular weight alcohol; and (6) from 0 to less than 10 mole percent, relative to the source of boron, of an overbasing acid, other than the source of boron; and (B) heating the reaction product of (A) to a temperature above the distillation temperatures of (4) and (5) to distill (4), (5) and water of reaction, wherein no additional water is added in the process.

7 Claims, No Drawings

US 7,964,611 B2

PROCESS FOR MAKING ALKALINE EARTH METAL BORATED SULFONATES

This application is a divisional of U.S. Ser. No. 11/292,404 filed Nov. 30, 2005 which is herein incorporated by reference.

BACKGROUND OF THE INVENTION

1. Field of the Invention

The present invention is directed to an improved process for making alkaline earth metal borated sulfonates.

Preventing and/or reducing wear, as well as improving friction properties, are very important properties of lubricating oil compositions. Boron-containing additives, especially alkaline earth metal borated sulfonates, have been found not only to have excellent anti-friction properties when employed in lubricating oil compositions but also to provide detergent, anti-rust, anti-corrosion, and extreme pressure properties.

The present invention is directed to the discovery of an improved method of making alkaline earth metal borated sulfonates.

2. Background Art

Inoue et al., U.S. Pat. No. 4,683,126, discloses a method for producing an alkaline earth metal borate dispersion comprising two steps. The first step comprises reacting at 20°-100° C. a mixture of the following ingredients (A) to (E): (A) 100 parts by weight of the oil-soluble neutral sulfonate of an alkaline earth metal, (B) 10-100 parts by weight of the hydroxide or oxide of an alkaline earth metal, (C) boric acid in an amount which is 0.5-6.5 times in mol that of the ingredient (B), (D) 5-50 parts by weight of water, and (E) 50-200 parts by weight of a dilution solvent. The second step comprises heating the resulting reaction mixture of the first step to 100°-200° C. to remove the water and a part of the dilution solvent as required.

Hellmuth et al., U.S. Pat. No. 3,480,548 discloses a lubricating oil composition prepared by reacting a lubricating oil dispersion of an alkaline earth metal carbonate and alkaline earth metal hydrocarbon sulfonate with a boron compound selected from the group consisting of boric acids, boron oxides, and aqueous alkyl esters of boric acids.

Hellmuth et al., U.S. Pat. No. 3,679,584 discloses a process for increasing the alkaline earth metal ratio of an alkaline earth metal carbonate overbased alkaline earth metal sulfonate lubricating oil composition comprising introduction into a lubricating oil medium containing a colloidal-like dispersion of an alkaline earth metal carbonate overbased alkaline earth metal sulfonate, an alkaline earth metal hydroxide and boric acid and subsequently contacting the resultant mixture with carbon dioxide.

Fischer et al., U.S. Pat. No. 4,744,920 discloses a carbonated overbased product that has been borated. Specifically, the process comprises (a) mixing an overbased sulfonate and any required inert liquid medium, (b) borating the mixture (a) with a borating agent at a temperature less than at which substantial foaming occurs, (c) raising the temperature of the mixture (b) to that temperature in excess of the boiling point of water within the mixture (b), (d) separating substantially all of the water from the reaction mixture (c) while retaining substantially all of the carbonate in the mixture (c) and, (e) recovering the product (d) as high carbonate content borated product.

Schlicht, U.S. Pat. No. 4,965,003 discloses a process for preparing a borated, overbased oil-soluble metal detergent additive for lubricants, said process comprising (a) mixing a metal salt dissolved in a hydrocarbon solvent with a metal base and a polar solvent; (b) treating said metal salt mixture at a temperature ranging from about 10° C. to about 100° C. while passing an acid gas through the mixture; (c) filtering said treated mixture at a temperature of about 10° C. to about 100° C.; (d) adding a borating agent to said filtrate and reacting said filtrate for a period of about 0.25 to about 5.0 hours at a temperature ranging from about 15° C. to about 100° C.; (e) heating said borated mixture at a temperature sufficiently high to distill a major portion of the polar solvent and water therefrom; (f cooling the distilled borated mixture to below the boiling point of the remaining solvent and filtering said cooled filtrate mixture; and (g) stripping the cooled distilled filtrate mixture under a pressure ranging from about 10 to about 200 mm Hg at a temperature ranging from about 20° C. to about 150° C., thereby recovering the borated metal detergent additive.

Schlicht et al., U.S. Pat. No. 4,965,004 discloses (a) adding a borating agent to an overbased metal salt in the presence of a protic solvent and a hydrocarbon solvent and reacting for a period of about 0.25 to about 5.0 hours at a temperature ranging from about 15° C. to about 100° C.; (b) heating said borated metal salt mixture at a temperature sufficiently high to distill an amount of distillate equal to at least about 80 percent of the protic solvent fed; (c) cooling the distilled borated mixture to below the boiling point of the remaining solvent and filtering said cooled filtrate mixture; and (d) stripping the cooled distilled filtrate mixture under a pressure ranging from about 10 to about 200 mm Hg at a temperature ranging from about 20° C. to about 150° C., and recovering the borated metal detergent additive.

SUMMARY OF THE INVENTION

Accordingly, in its broadest embodiment, the present invention is directed to a process for preparing an alkaline earth metal borated sulfonate comprising:
  (a) reacting
    (i) at least one of an oil soluble sulfonic acid or alkaline earth sulfonate salt or mixtures thereof;
    (ii) at least one source of an alkaline earth metal; and
    (iii) at least one source of boron, in the presence of a mixture comprising
    (iv) at least one hydrocarbon solvent;
    (v) at least one low molecular weight alcohol; and
    (vi) from 0 to less than 10 mole percent, relative to the source of boron, of an overbasing acid, other than the source of boron; and
  (b) heating the reaction product of (a) to a temperature above the distillation temperatures of (iv) and (v) to distill (iv), (v) and water of reaction, wherein no additional water is added in the process.

DETAILED DESCRIPTION OF THE INVENTION

While the invention is susceptible to various modifications and alternative forms, specific embodiments thereof have been shown by way of example and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

The term "Total Base Number" or "TBN" refers to the amount of base equivalent to milligrams of KOH in 1 gram of sample. Thus, higher TBN numbers reflect more alkaline products and therefore a greater alkalinity reserve. For the purposes of this invention, TBN is determined by ASTM Test No. D2896.

It has been discovered that the borated sulfonate made by the process disclosed within results in low sediment.

Process for Preparing an Alkaline Earth Metal Borated Sulfonate

The present invention involves an improved process for preparing an alkaline earth metal borated sulfonate.

The process for preparing an alkaline earth metal borated sulfonate comprises
(a) reacting
  (i) at least one of an oil soluble sulfonic acid or alkaline earth sulfonate salt or mixtures thereof;
  (ii) at least one source of an alkaline earth metal; and
  (iii) at least one source of boron, in the presence of a mixture comprising
  (iv) at least one hydrocarbon solvent;
  (v) at least one low molecular weight alcohol; and
  (vi) from 0 to less than 10 mole percent, relative to the source of boron, of an overbasing acid, other than the source of boron; and
(b) heating the reaction product of (a) to a temperature above the distillation temperatures of (iv) and (v) to distill (iv), (v) and water of reaction, wherein no additional water is added in the process.

Hydrocarbon Solvent

The hydrocarbon solvent which may be used in the present process may be selected from the group consisting of n-pentane, n-hexane, cyclohexane, n-heptane, n-octane, isooctane, n-decane, benzene, toluene, xylene and mixtures thereof. Preferably, the hydrocarbon solvent is an aromatic solvent and is selected from the group of solvents consisting of xylene, benzene and toluene. The most preferred aromatic solvent is xylene.

Low Molecular Weight Alcohol

The low molecular weight alcohol must have a boiling point sufficiently low so that it may be easily distilled off after the reaction has occurred. Typically, the low molecular weight alcohol will have from about 1 to about 13 carbon atoms and a molecular weight no higher than about 200. In one embodiment, the low molecular weight alcohol is a low molecular weight monohydric alcohol. In a more preferred embodiment the low molecular weight monohydric alcohol which may be used in the present process may be selected from the group consisting of (C1-C13) alcohols and glycol monoethers and monoesters. Preferably, the low molecular weight alcohol is a monohydric alcohol selected from the group consisting of methanol, ethanol, propanol, isooctanol, cyclohexanol, cyclopentanol, isobutyl alcohol, benzyl alcohol, beta-phenyl-ethyl alcohol, 2-ethylhexanol, dodecanol, tridecanol, 2-methylcyclohexanol, monomethyl ether of ethylene glycol, monobutyl ether of ethylene glycol, sec-pentyl alcohol, and tert-butyl alcohol. The most preferred low molecular weight monohydric alcohol is methanol.

In a further embodiment, the low molecular weight alcohol is a polyhydric alcohol; in a preferred embodiment, the polyhydric alcohol is a dihydric alcohol, such as ethylene glycol.

Oil Soluble Sulfonic Acid or Alkaline Earth Metal Sulfonate Salt

In the present invention, either an oil soluble sulfonic acid or an oil soluble alkaline earth metal sulfonate salt is used in the process for preparing a borated sulfonate.

Sulfonic Acid

In one embodiment of the present invention, an oil soluble sulfonic acid may be used in the process for preparing a borated sulfonate. The sulfonic acid may be derived from sulfonating alkyl aromatics, especially alkylbenzene and alkyltoluene, such as linear alkylbenzene or alkyltoluene, branched alkylbenzene or alkyltoluene, or benzene or toluene having a polyalkenyl group (e.g., polyisobutene) with sulfuric acid, sulfur trioxide, chlorosulfonic acid or sulfamic acid. Sulfonic acid preparation is well known in the art.

In another embodiment of the present invention, the oil soluble sulfonic acid may be a polyalkylene sulfonic acid, especially a polyisobutene sulfonic acid. Sulfonic acids prepared from polyisobutenes are the subject of U.S. Pat. No. 6,410,491 which is incorporated herein by reference in its entirety and the sulfonate that is prepared from the sulfonic acid derived from polyisobutene is disclosed in U.S. Pat. No. 6,632,781 which is incorporated herein by reference.

Preferably, the sulfonic acid is obtained by the sulfonation of a mixture of primarily mono alkylbenzenes which are obtained from the alkylation of benzene by a mixture of heavy alpha linear olefins having from about 20 to about 24 carbon atoms.

In another embodiment the sulfonic acid is obtained by the sulfonation of a mixture of primarily mono alkyltoluene which are obtained from the alkylation of toluene by a mixture of heavy alpha linear olefins having from about 20 to about 24 carbon atoms.

Alkylbenzene may be derived from the alkylation of an aromatic compound wherein the alkylation is the reaction of a linear olefin which comprises at least 16 carbon atoms and an aromatic compound in the presence of a Lewis Acid. Preferably, the olefin is a normal alpha olefin that has from about 18 carbon atoms to about 26 carbon atoms. Alkylated aromatics, the process of which is well known in the art, may be derived from numerous processes including, but not limited to, the processes disclosed in US Patent Application Publication Nos. US 2005/0202954, US 2005/0203323, and US 2005/0203322.

Alkaline Earth Metal Sulfonate Salt

In another embodiment of the present invention, an alkaline earth metal sulfonate salt may be used in the process to prepare a borated sulfonate. The alkaline earth metal sulfonate salt may be derived from reacting a source of an alkaline earth metal with an alkylbenzene sulfonic acid. Preferably, when employing a linear alkylbenzene, the synthetic linear alkylbenzene sulfonic acid produced, therefrom, may be neutralized with a source of an alkaline earth metal. In a more preferred embodiment, the linear alkylbenzene sulfonic acid is neutralized with an alkaline earth metal hydroxide, such as, but not limited to, calcium hydroxide or magnesium hydroxide.

An important feature of this invention is that the alkaline earth metal sulfonate salt, if used, contains an amount of overbasing acid other than the source of boron, such that the product borated sulfonate contains from 0 to less than 10 mole percent, relative to the source of boron, of an overbasing acid, other than the source of boron. In a preferred embodiment the alkaline earth metal sulfonate salt does not contain an overbasing acid other than the source of boron. Preferably the alkaline earth metal sulfonate salt is a neutral alkaline earth metal sulfonate salt. Preferably the alkaline earth metal sulfonate salt has a TBN of from about 0 to about 50.

The sulfonate salts are those having a substantially oleophilic character and which are formed from organic materials. Organic sulfonates are well known materials in the lubricant and detergent arts. The sulfonate compound should contain on average from about 10 to about 40 carbon atoms, preferably from about 12 to about 36 carbon atoms and preferably from about 14 to about 32 carbon atoms.

Typically, the sulfonate is an alkyl aromatic sulfonate wherein the alkyl group is preferably derived from a normal alpha olefin. More preferred, the aromatic moiety is benzene or toluene and the alkyl group has from about 20 to about 24 carbon atoms. The most preferred sulfonate composition is a monosulfonated alkylated benzene.

Alkaline Earth Metal

A source of an alkaline earth metal is also reacted with the aforementioned compounds (i.e., at least one oil soluble sulfonic acid or alkaline earth metal sulfonate salt or mixtures thereof) in the presence of a mixture comprising a hydrocarbon solvent and a low molecular weight alcohol. Preferably, the alkaline earth metal used in the reaction of the present invention is an alkaline earth metal hydroxide or oxide. The most preferred source of alkaline earth metal is calcium hydroxide (lime).

Source of Boron

A source of boron is also reacted with the aforementioned compounds (i.e., at least one oil soluble sulfonic acid or alkaline earth metal sulfonate salt or mixtures thereof, and source of an alkaline earth metal) in the presence of a mixture comprising a hydrocarbon solvent and a low molecular weight alcohol. Boron sources include polymers of boric acid, boron anhydride, boron esters, and similar materials. The most preferred source of boron is orthoboric acid.

Overbasing Acid

The term "overbasing acid," as used herein, refers to an acid capable of providing an oil-soluble metal sulfonate with greater than a stoichiometric amount of metal to sulfonic acid. The most common overbasing acid is carbon dioxide; other overbasing acids include sulfur dioxide and sulfur trioxide. The acid itself may be part of the overbasing process, or alternatively a source of an overbasing acid such as ethylene carbonate may be used to introduce the overbasing acid.

Process and Diluent Oils

If the borated sulfonate is viscous, an inert liquid medium may be employed to reduce the viscosity. The inert liquid medium can also serve to disperse the product and to facilitate mixing of the ingredients. A preferred inert liquid medium is lubricating oil. As disclosed in Fuels and Lubricants Handbook, edited by George E. Totten, p. 199 (2003), a lubricating oil or "base fluid can be of mineral origin, synthetic chemical origin or biological origin. While mineral oil basestocks [are derived] from petroleum fractionation, synthetic basestocks are manufactured through transformations of petroleum-derived organic chemicals. Partly synthetic (semisynthetic) basestocks are compatible mixtures of mineral oil and synthetic basestocks." Basestocks of biological origin are derived from vegetable and animal oils.

The inert liquid medium may be omitted where, for example, the product is extruded. In such cases mechanical mixing replaces the need for a solvent.

Foam inhibitors and other processing aids may also be added.

Process—Neutralization of Sulfonic Acid

In a typical process of the present invention, hydrocarbon solvent is first premixed with a low molecular weight alcohol and a source of an alkaline earth metal. Generally this pre-mixing is done near ambient temperatures, i.e. at about 15-40° C. Sulfonic acid is next added with agitation. Typically, sulfonic acid is added over a period of time wherein the temperature ranges from about 20° C. to about 40° C. Due to the heat of reaction, the temperature increases to from about 20° C. to about 55° C. The mixture is held for approximately 5 to 20 minutes at from about 40° C. to about 50° C. to ensure that the sulfonic acid is adequately neutralized by the source of alkaline earth metals to make a neutral alkaline earth metal sulfonate. If the alkaline earth sulfonate salt is used instead of the sulfonic acid this neutralization step is omitted.

The source of boron, such as boric acid, is added over a period of from about 5 minutes to about 20 minutes, while the temperature was maintained at from about 30° C. to about 50° C. The reaction is held at from about 30° C. to about 50° C. for from about 5 minutes to about 15 minutes. The reaction mixture may be held at an intermediate temperature of from about 70° C. to about 80° C. to reduce sediment in the final product. Methanol, water and xylene are then eliminated through separation methods that are well known in the art, such as distillation. Typically, a distillation step is used in which the above reaction mixture is heated to from about 125° C. to about 140° C. Typically, a diluent oil, such as 100N oil, will be employed and will be added to the mixture before all the hydrocarbon solvent is distilled. The un-reacted lime and boric acid are eliminated by conventional methods, such as centrifugation or filtration. The final product will have a typical base number of from about 10 to about 250 mg KOH/g.

When employed, the overbasing acid other than the source of boron may be introduced with the alkaline earth metal sulfonate salt, or introduced in situ during the reaction, or introduced after the reaction. In a preferred embodiment, the present process does not employ an overbasing acid other than the source of boron.

In a preferred embodiment of the present invention, the borated sulfonate is a borated calcium sulfonate.

The borated sulfonate of this process contains from 0 to less than 10 mole percent, relative to the source of boron, of an overbasing acid, other than the source of boron. In a preferred embodiment the process for preparing the alkaline earth metal borate sulfonate contains no overbasing acid, such as carbon dioxide, sulfur oxides etc., other than the source of boron. Additionally, although water may be a by-product of the reaction, no water is added to the reaction mixture.

In a preferred embodiment of the present invention the weight ratio of low molecular weight alcohol to source of an alkaline earth metal is at least 0.2, preferably at least 0.35, more preferably at least 0.5. Most preferably, the weight ratio of low molecular weight alcohol to source of an alkaline earth metal is at least 0.65.

The boron content of the sulfonates employed in the present invention is from about 3.0 wt % to about 5.0 wt %. More preferred the amount of boron in the sulfonate is from about 3.5 wt % to about 4.5 wt %. Most preferred the amount of boron in the sulfonate is from about 3.7 wt % to about 4.3 wt %. The water content of the borated sulfonate is typically less than 1.0% by weight. If the separation does not occur during processing, then during storage, the boron content may be diminished by having unacceptably high levels of water in the sulfonate product. Preferably, the water content of the sulfonate product is less than 1.0% by weight and more preferably less than 0.50% by weight.

The invention is further illustrated by the following examples, which set forth particularly advantageous method embodiments. While the examples are provided to illustrate the present invention, they are not intended to limit it.

EXAMPLES

Example A

Sulfonic Acid Preparation

In a typical preparation benzene is alkylated with a mixture of C20-C24 heavy alpha linear olefins thereby producing a mixture of monoalkylbenzenes. Sulfur is burned to produce SO2 which is converted to SO3 using V2O5 catalyst in a fixed bed reactor.

Sulfonic acid is obtained by the sulfonation of a mixture of monoalkylbenzenes with SO3 at a charge mole ratio of SO3/alkylate of 0.85 to 1.00. The alkylate at 55-60O C is contacted with a SO3/air mixture in a falling film sulfonator.

Example 1

To a 1 liter glass reactor, equipped with a heating mantle and mixer, was added 464 grams of mixed xylenes solvent. To the same reactor, 62 grams of methanol was added, followed by 52 grams of lime (calcium hydroxide). To the above mixture, which was at ambient temperature, 150 grams of sulfonic acid (as prepared in Example A) was added. The temperature increased to 30 degrees C. 74 grams boric acid was then added to the reactor. The temperature increased to 35 degrees C. The reactor was then heated to 127 degrees C. over a period of 2 hours, to remove the water and methanol as well as some xylene. 80 grams Group I base oil was added to the reactor. The sediment in the reactor was measured at 1.8 vol %. The reactor was then heated to 170 degrees C. and 1 PSIA to distill the xylene. The resulting product had an amount of sediment of 3.6 vol %.

The product was then filtered and had the following characteristics:
Calcium: 9.4 wt %
Boron: 4.1 wt %
BN: 173
Viscosity 390 cST at 100 degrees C.

Example 2

To a 1 liter glass reactor, which is equipped with a heating mantle and mixer, was added 234 grams of mixed xylenes solvent. To the same reactor, 50 grams of lime (calcium hydroxide) was added. To the above mixture, which was at ambient temperature, 150 grams of sulfonic acid (as prepared in Example A) was added. The temperature increased to 40 degrees C. The reactor was cooled to 18 degrees C. and 974 grams of boric acid was added. 62 grams of methanol was added to the reactor and the temperature increased to 32 degrees C.

Over a 2 hour period, the reactor was heated to 127 degrees C. in order to remove water, methanol and some xylene. 80 grams of Group I base oil was added to the reactor and the amount of sediment was measured at 2.0 vol %. the reactor was then heated to 170 degrees C. and 1 PSIA to distill the xylene. The resulting product had an amount of sediment of 3.2 vol %.

Example 3

To a 1 liter glass reactor, which is equipped with a heating mantle and mixer, was added 406 grams of mixed xylenes solvent. To the same reactor, 50 grams of lime (calcium hydroxide) was added. To the above mixture, which was at ambient temperature, 150 grams of sulfonic acid (as prepared in Example A) was added. The temperature increased to 44 degrees C. The reactor was cooled to 18 degrees C. and 74 grams of boric acid was added. 62 grams of methanol was added to the reactor which caused the temperature to increase to 32 degrees C. Over a 2 hour period, the reactor was heated to 127 degrees C. in order to remove water, methanol and some xylene. 80 grams of Group I base oil was added to the reactor and the amount of sediment was measured at 1.8 vol %. The reactor was then heated to 170 degrees C. and 1 PSIA to distill the xylene. The resulting product had an amount of sediment of 3.6 vol %.

Example 4

To a 1 liter glass reactor, which was equipped with a heating mantle and mixer, was added 300 grams of mixed xylenes solvent. To the same reactor, 50 grams of lime (calcium hydroxide) was added. To the above mixture, which was at ambient temperature, 150 grams of sulfonic acid (as prepared in Example A) was added. The temperature increased to 44 degrees C. The reactor was cooled to 18 degrees C. and 74 grams of boric acid was added. 42 grams of methanol was added to the reactor which caused the temperature to increase to 32 degrees C. Over a 2 hour period, the reactor was heated to 127 degrees C. in order to remove water, methanol and some xylene. 80 grams of Group I base oil was added to the reactor and the amount of sediment was measured at 1.8 vol %. The reactor was then heated to 170 degrees C. and 1 PSIA to distill the xylene.

The resulting product had an amount of sediment of 3.6 vol %.

Example 5

To a 1 liter glass reactor, which was equipped with a heating mantle and mixer, was added 300 grams of mixed xylenes solvent. To the same reactor, 47 grams of lime (calcium hydroxide) was added. To the above mixture, which was at ambient temperature, 150 grams of sulfonic acid (as prepared in Example A) was added. The temperature increased to 43 degrees C. The reactor was cooled to 18 degrees C. and 74 grams of boric acid was added. 30 grams of methanol was added to the reactor which caused the temperature to increase to 24 degrees C.

Over a 2 hour period, the reactor was heated to 127 degrees C. in order to remove water, methanol and some xylene. 80 grams of Group I base oil was added to the reactor and the amount of sediment was measured at 2.8 vol %. The reactor was then heated to 170 degrees C. and 1 PSIA to distill the xylene.

The resulting product had an amount of sediment of 4.8 vol %.

Example 6

To a 1 liter glass reactor, which was equipped with a heating mantle and mixer, was added 300 grams of mixed xylenes solvent. To the same reactor, 50 grams of lime (calcium hydroxide) was added. To the above mixture, which was at ambient temperature, 150 grams of sulfonic acid (as prepared in Example A) was added. The temperature increased to 43 degrees C. The reactor was cooled to 18 degrees C. and 74 grams of boric acid was added. 20 grams of methanol was added to the reactor which caused the temperature to increase to 29 degrees C.

Over a 2 hour period, the reactor was heated to 127 degrees C. in order to remove water, methanol and some xylene. 80 grams of Group I base oil was added to the reactor and the amount of sediment was measured at 10.4 vol %. The amount of sediment in the final product was too great too measure.

Comparative Example 1

This comparative Example was run according to the method of Inoue et al., U.S. Pat. No. 4,683,126. To a 1 liter glass reactor, which was equipped with a heating mantle and mixer, was added 234 grams of mixed xylenes solvent. To the same reactor, 50 grams of lime (calcium hydroxide) was added. To the same reactor, 150 grams of sulfonic acid (as prepared in Example A) was added.

74 grams of boric acid was added at 18 degrees C. Next, 15 grams of water was added. The reactor was then heated to 60 degrees C. and another 15 grams of water was added. The reactor was then held at 79 degrees C. for one hour. The sediment was then measured at 40 vol %. The reactor was heated to 127 degrees C. over a period of 100 minutes. The amount of sediment at the end of the reaction was 48%. This amount of sediment indicates that the lime was barely, if at all incorporated in this reaction.

TABLE 1

| Example | Methanol/lime wt-% ratio | Sediment at 127° C. | Final sediment, wt-% |
|---|---|---|---|
| 1 | 1.24 | 1.8 | 3.6 |
| 2 | 1.24 | 2.0 | 3.2 |
| 3 | 1.24 | 0.8 | 3.6 |
| 4 | 0.83 | 1.8 | 3.6 |
| 5 | 0.62 | 2.8 | 4.8 |
| 6 | 0.41 | 10.4 | — |
| Comparative Example 1 | 0 | 40 | 48 |

This comparison shows that the use of added water in the process to make a borated sulfonate leads to such an increase in sediment as to make the process untenable. In addition, there appears to be a threshold amount of low molecular weight alcohol that, when added to the reaction mixture, yields a final product that has a decreased amount of sediment.

It is understood that although modifications and variations of the invention can be made without departing from the spirit and scope thereof, only such limitations should be imposed as are indicated in the appended claims.

What is claimed is:

1. An alkaline earth metal borated alkyltoluene sulfonate prepared by the process comprising:
   (a) reacting
   (i) at least one of an oil soluble alkyltoluene sulfonic acid, an alkaline earth metal alkyltoluene sulfonate salt, or mixtures thereof;
   (ii) at least one source of alkaline earth metal;
   (iii) at least one source of boron, in the presence of a mixture comprising:
      (1) at least one hydrocarbon solvent;
      (2) at least one low molecular weight alcohol; and
   (iv) from 0 to less than 10 mole percent, relative to the source of boron, of an overbasing acid, other than the source of boron; and
   (b) heating the reaction product of (a) to a temperature above the distillation temperatures of the hydrocarbon solvent and the low molecular weight alcohol to distill the hydrocarbon solvent, the alcohol and the water generated from the reaction, wherein no additional water is added in the process.

2. The alkaline earth metal borated alkyltoluene sulfonate according to claim 1, wherein the alkyltoluene sulfonic acid or sulfonate salt is a linear alkyltoluene sulfonic acid or sulfonate salt.

3. The alkaline earth metal borated alkyltoluene sulfonate according to claim 1, wherein the alkyltoluene sulfonic acid or sulfonate salt is a branched alkyltoluene sulfonic acid or sulfonate salt.

4. The alkaline earth metal borated alkyltoluene sulfonate according to claim 1, wherein the alkyltoluene sulfonic acid or sulfonate salt is a polyalkenyl toluene sulfonic acid or sulfonate salt.

5. The alkaline earth metal borated alkyltoluene sulfonate according to claim 2, wherein the linear alkyl group of the linear alkyltoluene sulfonic acid or sulfonate salt comprises at least 16 carbon atoms.

6. The alkaline earth metal borated alkyltoluene sulfonate according to claim 5, wherein the linear alkyl group of the linear alkyltoluene sulfonic acid or sulfonate salt comprises about 16 to about 28 carbon atoms.

7. The alkaline earth metal borated alkyltoluene sulfonate according to claim 6, wherein the linear alkyl group of the linear alkyltoluene sulfonic acid or sulfonate salt comprises about 20 to about 24 carbon atoms.

* * * * *